US007927797B2

(12) United States Patent
Nobile et al.

(10) Patent No.: US 7,927,797 B2
(45) Date of Patent: Apr. 19, 2011

(54) NUCLEIC ACID AMPLIFICATION WITH CONTINUOUS FLOW EMULSION

(75) Inventors: John R. Nobile, Fairfield, CT (US); William L. Lee, Madison, CT (US); John H. Leamon, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 253 days.

(21) Appl. No.: 11/045,678

(22) Filed: Jan. 28, 2005

(65) Prior Publication Data

US 2005/0227264 A1 Oct. 13, 2005

Related U.S. Application Data

(60) Provisional application No. 60/540,016, filed on Jan. 28, 2004.

(51) Int. Cl.
 C12Q 1/68 (2006.01)
 C12P 19/34 (2006.01)
 F02M 47/02 (2006.01)
(52) U.S. Cl. .............. 435/6; 435/91.2; 239/88
(58) Field of Classification Search .............. None
See application file for complete search history.

(56) References Cited

U.S. PATENT DOCUMENTS

| 5,176,203 | A | 1/1993 | Larzul | 165/61 |
| 5,225,332 | A * | 7/1993 | Weaver et al. | 435/29 |
| 5,270,183 | A | 12/1993 | Corbett et al. | 435/91.2 |
| 5,498,392 | A | 3/1996 | Wilding et al. | 422/68.1 |
| 5,587,128 | A | 12/1996 | Wilding et al. | 422/50 |
| 5,720,923 | A | 2/1998 | Haff et al. | 422/68.2 |
| 5,726,026 | A | 3/1998 | Wilding et al. | 435/7.21 |
| 5,779,977 | A | 7/1998 | Haff et al. | 422/68.1 |
| 5,827,480 | A | 10/1998 | Haff et al. | 422/68.1 |
| 5,891,477 | A * | 4/1999 | Lanza et al. | 424/501 |
| 5,939,312 | A | 8/1999 | Baier et al. | 435/287.2 |
| 5,989,892 | A | 11/1999 | Nishimaki et al. | 435/252.1 |
| 6,023,540 | A | 2/2000 | Walt et al. | 385/12 |

(Continued)

FOREIGN PATENT DOCUMENTS

EP 1 522 581 4/2005

(Continued)

OTHER PUBLICATIONS

Obeid et al., Microfabricated Device for DNA and RNA Amplification by Continuous-Flow Polymerase Chain Reaction and Reverse Transcription-Polymerase Chain Reaction with Cycle Number Selection, Anal. Chem. 2003, 75; 288-295.*

(Continued)

Primary Examiner — Mark Staples
(74) Attorney, Agent, or Firm — Ivor R. Elrifi; Mintz Levin Cohn Ferris Glovsky and Popeop PC

(57) ABSTRACT

Embodiments of the present invention are directed to methods and devices/systems for amplifying genetic material and may include providing a water-in-oil emulsion in a continuous flow. The emulsion may include a plurality of water droplets comprising microreactors. Each of the plurality of microreactors may include a single bead capable of capturing a nucleic acid template, a single species nucleic acid template and sufficient reagents to amplify the copy number of the nucleic acid template. The method also includes flowing the emulsion across a first temperature zone and a second lower temperature zone to thermally process the microreactors to amplify the nucleic acid template by polymerase chain reaction.

20 Claims, 10 Drawing Sheets

U.S. PATENT DOCUMENTS

| | | | |
|---|---|---|---|
| 6,033,880 A | 3/2000 | Haff et al. | 435/91.1 |
| 6,045,676 A | 4/2000 | Mathies et al. | 204/603 |
| 6,132,580 A | 10/2000 | Mathies et al. | 204/453 |
| 6,143,152 A | 11/2000 | Simpson et al. | 204/451 |
| 6,174,675 B1 | 1/2001 | Chow et al. | 435/6 |
| 6,184,012 B1 | 2/2001 | Neri et al. | 435/188 |
| 6,184,029 B1 | 2/2001 | Wilding et al. | 435/287.1 |
| 6,207,031 B1 | 3/2001 | Adourian et al. | 204/451 |
| 6,258,858 B1 | 7/2001 | Nakajima et al. | 516/73 |
| 6,261,431 B1 | 7/2001 | Mathies et al. | 204/601 |
| 6,266,459 B1 | 7/2001 | Walt et al. | 385/12 |
| 6,284,525 B1 | 9/2001 | Mathies et al. | 435/287.2 |
| 6,303,309 B1 | 10/2001 | Jurinke et al. | 435/6 |
| 6,303,343 B1 | 10/2001 | Kopf-Sill | 435/91.1 |
| 6,310,354 B1 | 10/2001 | Hanninen et al. | 250/458.1 |
| 6,361,671 B1 | 3/2002 | Mathies et al. | 204/452 |
| 6,436,355 B1 | 8/2002 | Lee et al. | 422/199 |
| 6,489,103 B1 | 12/2002 | Griffiths et al. | 435/6 |
| 6,551,841 B1 | 4/2003 | Wilding et al. | 436/518 |
| 6,586,233 B2 | 7/2003 | Benett et al. | 435/286.5 |
| 6,602,473 B1 | 8/2003 | Northrup | 422/102 |
| 6,613,560 B1 | 9/2003 | Tso et al. | 435/287.2 |
| 6,635,226 B1 | 10/2003 | Tso et al. | 422/129 |
| 6,660,517 B1 | 12/2003 | Wilding et al. | 435/289.1 |
| 6,887,664 B2 | 5/2005 | Chen et al. | 435/6 |
| 6,953,676 B1 | 10/2005 | Wilding et al. | 435/91.2 |
| 7,005,292 B2 | 2/2006 | Wilding et al. | 435/287.1 |
| 7,018,830 B2 | 3/2006 | Wilding et al. | 435/287.1 |
| 2001/0020588 A1 | 9/2001 | Adourian et al. | 204/451 |
| 2001/0036632 A1 | 11/2001 | Yu et al. | 435/6 |
| 2002/0001675 A1 | 1/2002 | Tisone | 427/244 |
| 2002/0068357 A1 | 6/2002 | Mathies et al. | 435/287.2 |
| 2002/0119459 A1* | 8/2002 | Griffiths | 435/6 |
| 2002/0168279 A1 | 11/2002 | Yamamoto et al. | 418/104 |
| 2002/0172980 A1 | 11/2002 | Phan et al. | 435/7.1 |
| 2003/0207266 A1 | 11/2003 | Chen et al. | 435/6 |
| 2003/0214994 A1 | 11/2003 | Schicke et al. | 374/11 |
| 2004/0053254 A1 | 3/2004 | Wangh et al. | 435/6 |
| 2005/0079510 A1 | 4/2005 | Berka et al. | 435/6 |
| 2005/0130173 A1 | 6/2005 | Leamon et al. | 435/6 |
| 2005/0202489 A1 | 9/2005 | Cho et al. | 435/6 |
| 2006/0163385 A1 | 7/2006 | Link et al. | 239/424 |
| 2007/0003442 A1 | 1/2007 | Link et al. | 422/99 |

FOREIGN PATENT DOCUMENTS

| | | |
|---|---|---|
| EP | 1 522 582 | 4/2005 |
| WO | WO 89/10566 * | 11/1989 |
| WO | WO 97/40141 | 10/1997 |
| WO | WO 99/02671 | 1/1999 |
| WO | WO 00/40712 | 7/2000 |
| WO | WO 01/18244 | 3/2001 |
| WO | WO 02/22869 A1 | 3/2002 |
| WO | WO 02/103011 | 12/2002 |
| WO | WO 02/103363 | 12/2002 |
| WO | WO 03/044187 | 5/2003 |
| WO | WO 2004/069849 A2 | 8/2004 |
| WO | WO 2004/083443 A1 | 9/2004 |

OTHER PUBLICATIONS

Fan et al., Dynamic DNA Hybridization on a Chip Using Paramagnetic Beads,Anal. Chem. 1999, 71, 4851-4859.*

Kopp et al., Chemical Amplification: Continuous-Flow PCR on a Chip, Science, vol. 280, May 15, 1998, pp. 1046-1048.*

Bruckner-Lea et al., Renewable microcolumns for automated DNA purification and flow-through amplification: from sediment samples through polymerase chain reaction,Analytica Chimica Acta 21616 (2001) 1-12.*

Nisisako et al., Rapid Preparation of Monodispersed Droplets With Confluent Laminar Flows, 03-7744-3/03/$17.08, 2003, IEEE, pp. 331-334.*

Bruno et al., Development of an Immunomagnetic Assay System for Rapid Detection of Bacteria and Leukocytes in Body Fluids, Journal of Molecular Recognition, vol. 9.474479 (1996).*

Schneegass et al., Flow-through polymerase chain reactions in chip thermocyclers, Reviews in Molecular Biotechnology 82 (2001) 101-121.*

Katsura et al., Indirect mincromanipulation of single molecules in water-in-oil emulsion, Electrophoresis 2001, 22, 289-293.*

Chiou J et al.: "A Closed-Cycle Capillary Polymerase Chain Reaction Machine" Analytical Chemistry, American Chemical Society, Columbus, US, vol. 73, No. 9, May 1, 2001, pp. 2018-2021, XP-001071442.

Schneegass I et al: "Miniaturized Flow-Through PCR With Different Tmeplate Types in a Silicon Chip Thermocycler" Lab on a Chip, Royal Society of Chemistry, Cambridge, GB, vol. 1, No. 1, Sep. 2001, pp. 42-49, XP-009030439.

Nakano Michihiko et al: "Single-Molecule PCR Using Water-in-Oil Emulsion.", Journal of Biotechnology, vol. 102, No. 2, Apr. 24, 2003, pp. 117-124, XP-002327328.

Kopp et al: "Chemical Amplification: Continuous Flow PCR on a Chip", Science, American Associate for the Advancement of Science, US, vol. 280, May 15, 1998, pp. 1046-1048, XP-002107956.

Nakano Hideo et al: "High Speed Polymerase Chain Reaction in Constant Flow", Bioscience Biotechnology and Biochemistry, vol. 58, No. 2, 1994, pp. 349-352, XP-009047283.

Park N et al: "Cylindrical Compact Thermal-Cycling Device for Continuous-Flow Polymerase Chain Reaction" Analytical Chemistry, American Chemical Society. Columbus, US, vol. 75, No. 21, Nov. 1, 2003, pp. 6029-6033, XP-001047342.

Dressman Devin et al: "Transforming Single DNA Molecules Into Fluroescent Magnetic Particles for Detection and Enumeration of Genetic Variation." Proceedings of the National Academy of Sciences of the United States of America. Jul. 22, 2003, vol. 100, No. 15, pp. 8817-8822, XP-002327377.

Russom Aman et al: "Single-Nucleotide Polymorphism Analysis by Allele-Specific Extension of Fluorescently Labeled Nucleotides in a Microfluidic Flow-Through Device." Electrophoeresis, vol. 24, No. 1, Jan. 2003, pp. 158-161, XP-002327386.

Katsura Shinji et al: "Indirect Micromanipulation of Single Molecules in Water-in-Oil Emulsion" Electrophoresis, vol. 22, No. 2, Jan. 2002, pp. 289-293, XP-002327329.

Kawakatsu Takahiro et al: "Regular-Sized Cell Creation in Microchannel Emulsification by Visual Microprocessing Method" Journal of the American Oil Chemists' Society, vol. 74, No. 3, 1997, pp. 317-321, XP-001206295.

Lundeberg J et al: "Solid-Phase Technology: Magnetic Beads to Improve Nucleic Acid Detection and Analysis" Biotechnology Annual Review, vol. 1, No. 4, 1995, pp. 373-401, XP-008044959.

Lund V et al: "Assesment of Methods for Covalent Binding of Nucleic Acids to Magnetic Beads, Dynabeadstm, and the Characteristics Fo the Bound Nucleic Acids in Hybridization Reactions" Nucleic Acids Research, Oxford University Press, Surrey, GB, vol. 16, No. 22, 1988, XP-000195548.

Ghadessy et al "Directed Evolution of Polymerase Function by Compartmentalized Self-Replication", Apr. 10, 2001, pp. 4552-4557.

E.T. Lagally et al "Single-Molecule DNA Amplification and Analysis in an Integrated Microfluidic Device", Analytical Chemistry 2001, vol. 73, No. 3, Feb. 1, 2001, pp. 565-570.

Brody et al "A Self-Assembled Microlensing Rotational Probe", Jan. 4, 1999, vol. 74, No. 1, pp. 144-146, 1999 American Institute of Physics.

Bauer: "Advances in Cell Separation: Recent Developments in Counterflow Centrifugal Elutriation and Continuous Flow Cell Separation", Journal of Chromatography B. 722 (1999) 55-69.

Curcio et al: Continuous Segmented-Flow Polymerase Chain Reaction for High-Throughput Miniaturized DNA Amplification, Analytical Chemistry, vol. 75, No. 1, Jan. 1, 2003.

Griffiths et al: Directed Evolution of an Extremely Fast Phosphotriesterase by In Vitro Compartmentalisation, The EMBO Journal, vol. 22, No. 1 pp. 24-35, 2003.

Sepp et al: "Microbead Display by In Vitro Compartmentalisation: Selection for Binding Using Flow Cytometry", FEBS Letters 532 (2002) pp. 455-458.

Tawfik & Griffiths (1998). Nat Biotechnol 16: 652-656.

Andreadis et al. (2000), Nucleic Acids Research, 28:i-viii.

Ruzicka (2000), Analyst, 125:1053-1060.

Strizhkov et al. (2000), BioTechniques, 29:844-857.

* cited by examiner

PCR Solution & Beads

Flow PCR Thermal Processing System Schematic

800

US 7,927,797 B2

NUCLEIC ACID AMPLIFICATION WITH CONTINUOUS FLOW EMULSION

CLAIM TO PRIORITY AND RELATED APPLICATIONS

This application claims the benefit under 35 U.S.C. §119 (e) of U.S. provisional patent application No. 60/540,016, filed Jan. 28, 2004. This application is also related to the following application Nos. 60/443,471, filed Jan. 29, 2003; 60/465,071, filed Apr. 23, 2003; 60/476,313, filed Jun. 6, 2003; 60/476,504, filed Jun. 6, 2003; U.S. Ser. Nos. 60/476, 592, filed on Jun. 6, 2003; 60/476,602, filed Jun. 6, 2003; and 60/497,985, filed Aug. 25, 2003. All patent and patent applications in this paragraph are hereby fully incorporated by reference.

This application also incorporates by reference the following copending U.S. patent application Ser. Nos. 10/767,899, filed Jan. 28, 2004; 10/767,894, filed Jan. 28, 2004; and 10/767,779, filed Jan. 28, 2004.

FIELD OF THE INVENTION

Embodiments of the present invention relate to methods and systems for clonally amplifying nucleic acid templates from a single copy number to quantities amenable for sequencing, as well as methods and systems for continuous flow PCR using emulsion and solid support for immobilizing amplified nucleic acids.

BACKGROUND

The ability to amplify a plurality of nucleic acid sequences, such as a genomic library or a cDNA library, is critical given the current methods of sequencing. Current sequencing technologies require millions of copies of nucleic acid per sequencing reaction, therefore, amplification of the initial DNA is necessary before genomic sequencing. Furthermore, the sequencing of a human genome would require tens of millions of different sequencing reactions.

Current techniques and systems for in vitro genome amplification involve laborious cloning and culturing protocols that have limited the utility of genomic sequencing. Other techniques, such as PCR, while fast and reliable, are unable to amplify a mixture of different fragments of DNA a genome in a representative and clonal fashion.

While random primed PCR can be easily engineered to amplify a plurality of nucleic acids in one reaction, this method is not preferred because the amplified product will be a mixture of different DNA fragments from the library. In addition, in a random PCR environment starting with a plurality of fragments, some DNA sequences are preferentially amplified at the expense of other sequences such that the amplified product does not represent the starting material. This problem with PCR may be overcome if each individual member of a library is amplified in a separate reaction.

However, this approach may be impractical if many thousands of separate reaction tubes are required for the amplification process, as a genomic library or cDNA library may include more than 1,000,000 fragments. Individual amplification of each fragment of these libraries in separate, conventional reaction tube is not practical.

SUMMARY OF THE INVENTION

The present invention provides for methods and systems for amplifying a plurality of nucleic acids (e.g., each sequence of a DNA library, transcriptome, or genome) in a rapid and economical manner using, for example, a means for encapsulating a plurality of DNA samples effectively individually in a microcapsule of an emulsion (i.e., a "microreactor"), performing amplification of the plurality of encapsulated nucleic acid samples simultaneously, and releasing the amplified plurality of DNA from the microcapsules for subsequent reactions.

Preferably, in some embodiments of the invention, a plurality of such microreactors include at least one capture bead (and preferably a single bead). Each capture bead is preferably designed to have a plurality of oligonucleotides that recognize (i.e., are complementary to) a portion of a nucleic acid template, and the amplification copies of this template. It is preferred that any one capture bead contain only one unique nucleic acid species.

Embodiments of the present invention provide methods and systems for performing continuous flow amplification, specifically, encapsulated continuous flow amplification. Such embodiments may be used with thermal or isothermal amplification reactions, for example, PCR, rolling circle amplification, whole genome amplification, nucleic acid sequence-based amplification, and single strand displacement amplification. In preferred embodiments, the apparatus employs steady state heat generation and transfer elements and cross-flow emulsion droplet generation as described in detail herein.

Accordingly, in one embodiment of the invention, a method for amplifying genetic material includes providing a water-in-oil emulsion in a continuous flow wherein the emulsion comprises a plurality of water-based droplets comprising microreactors. The plurality of the microreactors may each include one or more species of nucleic acid templates, and sufficient reagents to amplify the copy number of one of the nucleic acid templates. The method may also include thermally processing the emulsion by flowing it across stationary controlled temperature zones to amplify nucleic acid templates by polymerase chain reaction.

In another embodiment of the present invention, an apparatus for amplifying genetic material includes at least one fluid delivery device, at least one first temperature zone to cycle a plurality of microreactors each including one or more species nucleic acid templates to a first temperature, at least one second temperature zone to cycle the plurality of microreactors to second temperature lower than the first temperature, a first conduit for flowing at least a stream of oil therein from a first reservoir and a second conduit for flowing at least a water based PCR solution from a second reservoir out of an orifice and into the first conduit creating a water-in-oil emulsion. The PCR solution upon entering the first conduit comprises a plurality of droplets comprising the microreactors for performing polymerase chain reactions. A plurality of the microreactors each include one or more species of nucleic acid template.

In another embodiment of the invention, a cross-flow emulsification apparatus includes a first inlet for receiving an oil flow from a first conduit, an outlet for directing a water-in-oil emulsion out of the apparatus, a second inlet for receiving a water based PCR amplification reaction mixture from a second conduit and an orifice for delivering PCR reaction mixture from the second conduit into the first conduit, to form a plurality of water-in-oil droplets comprising microreactors. A plurality of the microreactors each include one or more nucleic acid templates and sufficient PCR amplification reaction mixture to produce a plurality of copies of nucleic acid template.

In another embodiment of the present invention, an apparatus for amplifying genetic material includes a water-in-oil emulsion in a continuous flow wherein the emulsion comprises a plurality of water droplets comprising microreactors. A plurality of the microreactors may include a single bead capable of capturing one or more nucleic acid templates, and sufficient reagents to amplify the copy number of the one or more nucleic acid templates. The apparatus may also include thermal processing means for thermally processing the emulsion to amplify nucleic acid templates by polymerase chain reaction.

In another embodiment of the present invention an emulsion generator including an emulsion oil supply, at least one syringe including a body and a plunger for dispensing a mixture for emulsifying into the emulsion oil, a cross-flow emulsification device for emulsifying the mixture, the device including an input attached to the output of the syringe, a syringe pump including an actuator capable of oscillating the plunger of the at least one syringe micrometer distances at a predetermined frequency along a length of travel of the plunger within the syringe body of the at least one syringe.

In another embodiment of the present invention, a method for substantially reducing clogging of a nozzle in syringe pump includes providing a syringe pump having at least one syringe including a body, a plunger having a plunger axis and an exit nozzle, the body for dispensing a mixture of micron or less sized particles suspended in a medium, and oscillating the plunger of the syringe along the axis of the plunger for micrometer distances at a predetermined frequency along a length of travel of the plunger within the syringe body.

In another embodiment of the present invention, an emulsion generator includes an emulsion oil supply, at least one syringe including a body and a plunger for dispensing a mixture for emulsifying into the emulsion oil, a magnetically-attractive mixing element disposed in the body of the syringe, a cross-flow emulsification device for emulsifying the mixture, the device including an input attached to the output of the syringe and a device capable of moving an external magnetic force axially along body of the syringe while in close proximity to the syringe body.

In another embodiment of the present invention an emulsion generator includes an emulsion oil supply, at least one syringe including a body and a plunger for dispensing a mixture for emulsifying into the emulsion oil, a magnetically-attractive mixing element disposed in the body of the syringe, a cross-flow emulsification device for emulsifying the mixture, the device including an input attached to the output of the syringe and a rotating drum having a magnet helically wound along the surface of the drum. The surface of the drum is positioned adjacent the body of the syringe.

In another embodiment of the present invention, a syringe pump includes an area for receiving at least one syringe, where the syringe includes a body and a plunger having a plunger axis. The syringe may be used for dispensing a mixture for emulsification into an emulsion oil. The syringe pump may also include an actuator capable of oscillating the plunger of the at least one syringe along the plunger axis micrometer distances at a predetermined frequency along a length of travel of the plunger within body of the at least one syringe.

In another embodiment of the present invention, a syringe pump includes an area for receiving at least one syringe, where the syringe includes a body and a plunger having a plunger axis. The syringe may be used for dispensing a mixture for emulsification into emulsion oil. The syringe pump may also include a magnetically attractive mixing element disposed in the body of the syringe and a rotating drum having a magnet helically wound along the surface of the drum, wherein the surface of the drum is positioned adjacent the body of the syringe.

Other objects, advantages, features and benefits of the invention will become more readily apparent by reference to the attached drawings and following detailed description of the invention.

DETAILED DESCRIPTION OF INVENTION

Brief Overview of Bead Emulsion Amplification

Figure 1:
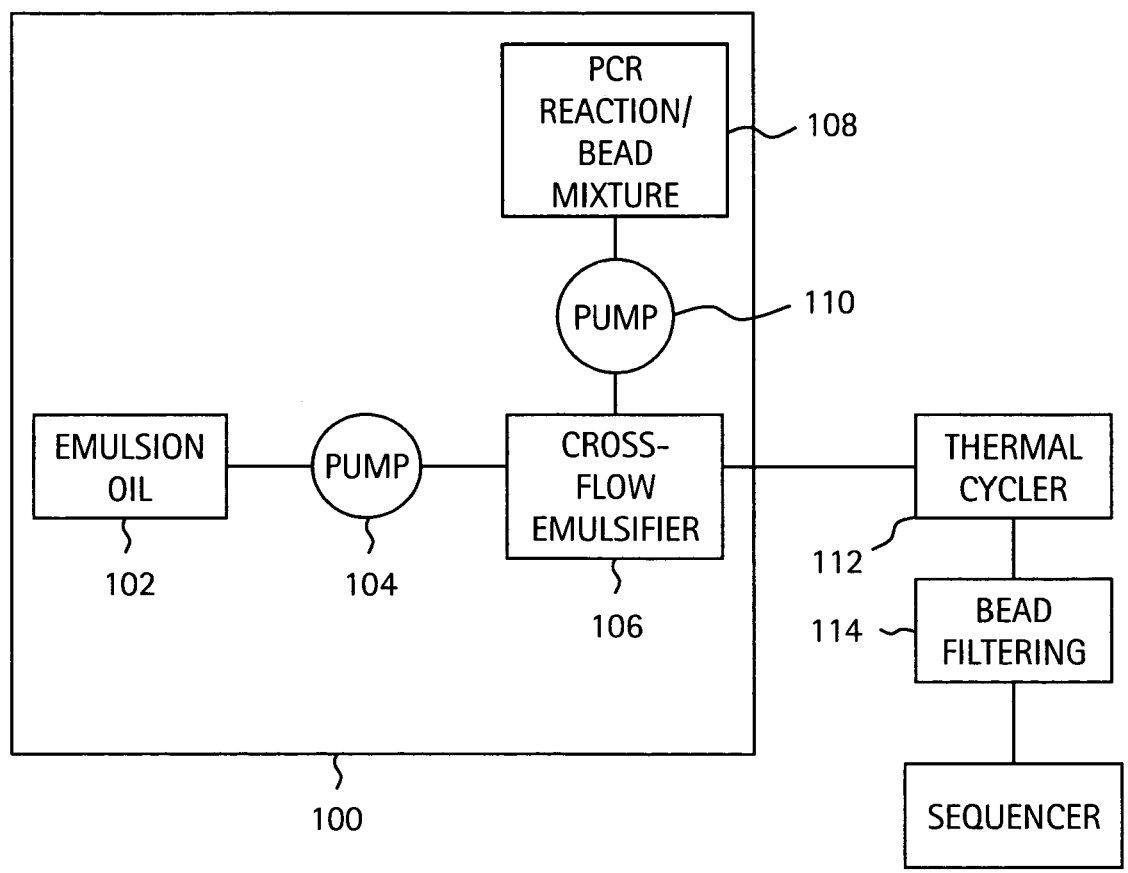
FIG. 1 is a system block diagram of a system for a PCR amplification system according to one of the embodiments of the present invention.

Bead emulsion amplification may be performed by attaching a template (e.g., DNA template) to be amplified, to a solid support, preferably in the form of a generally spherical bead. The bead is linked to a large number of a single primer species that is complementary to a region of the template DNA and the amplification copies of this template. Alternately, the bead is linked to chemical groups (e.g., biotin) that can bind to chemical groups (e.g., streptavidin) included on the template DNA and amplification copies of this template. See WO2004069849, herein incorporated by reference.

The beads are suspended in aqueous reaction mixture and then encapsulated in a water-in-oil emulsion. The template DNA may be bound to the bead prior to emulsification, or the template DNA is included in solution in the amplification reaction mixture.

The emulsion may be composed of discrete aqueous phase microdroplets (i.e., microreactors, see above), e.g., averaging approximately 60 to 200 μm in diameter, enclosed by a thermostable oil phase. Each microreactor contains, preferably, sufficient amplification reaction solution (i.e., the reagents necessary for nucleic acid amplification). An example of an amplification reaction solution would be a PCR reaction mixture (polymerase, salts, dNTPs; and may also preferably include a pair of PCR primers (primer A and primer B). In some cases, the template DNA is included in the reaction mixture. A subset of the microreactor population preferably includes microreactors having a single DNA bead preferably with an attached nucleic acid template. This subset of microreactors is the basis for the amplification in some of the preferred embodiments of the present application. In one embodiment, the remaining microreactors which do not contain template DNA will not participate in amplification.

PCR amplification and PCR primers may be present in an asymmetric ratio such as 8:1 or 16:1 (i.e., 8 or 16 of one primer to 1 of the second primer) to perform asymmetric PCR. The primer species that may be used in the lower concentration level is the same primer species that may be immobilized on the bead. This will increase the probability that an amplified copy of the template DNA will anneal to the bead. The ratio of PCR primers may also be substantially equal for normal PCR. The amplification reaction, such as PCR, may be performed using any suitable method.

After PCR, the beads containing the immobilized amplified DNA may be recovered. The emulsion may be broken to recover the beads. The immobilized product may be rendered single stranded by denaturing (by heat, pH etc.) which removes the complimentary A strand. The A primers are annealed to the A' region of immobilized strand, and the beads containing the immobilized strands are loaded with sequencing enzymes, and any necessary accessory proteins. The beads are then sequenced using recognized pyrophosphate techniques (described, e.g., in U.S. Pat. Nos. 6,274,320, 6,258,568 and 6,210,891, incorporated in toto herein by reference).

Template Design

In a preferred embodiment, the nucleic acid template to be amplified by bead emulsion amplification is a population of DNA such as, for example, a genomic DNA library or a cDNA library. It is preferred that each member of the DNA population have a common nucleic acid sequence at the first end and a common nucleic acid sequence at a second end. This can be accomplished, for example, by ligating a first adaptor DNA sequence to one end and a second adaptor DNA sequence to a second end of each member of the DNA population. The nucleic acid template may be of any size amenable to in vitro amplification (including the preferred amplification techniques of PCR and asymmetric PCR). In a preferred embodiment, the template is about 150 to 750 bp in size, such as, for example about 250 bp in size.

Binding Nucleic Acid Template to Capture Beads

A single stranded nucleic acid template to be amplified may be attached to a capture bead. The amplification copies of the nucleic acid template may also be attached to a capture bead. As non-limiting examples, these attachments may be mediated by chemical groups or oligonucleotides that are bound to the surface of the bead. The nucleic acid (e.g., the nucleic acid template, amplification copies, or oligonucleotides) may be attached to the solid support (e.g., a capture bead) in any manner known in the art.

According to the present invention, covalent chemical attachment of a nucleic acid to the bead can be accomplished by using standard coupling agents. For example, water-soluble carbodiimide can be used to link the 5'-phosphate of a DNA sequence to amine-coated capture beads through a phosphonamidate bond. Alternatively, specific oligonucleotides can be coupled to the bead using similar chemistry, and then DNA ligase can be used to ligate the DNA template to the oligonucleotide on the bead. Other linkage chemistries to join the oligonucleotide to the beads include the use of N-hydroxysuccinamide (NHS) and its derivatives, for example.

In an exemplary method, one end of a linker may contain a reactive group (such as an amide group) which forms a covalent bond with the solid support, while the other end of the linker contains a second reactive group that can bond with the oligonucleotide to be immobilized. In a preferred embodiment, the oligonucleotide is bound to the DNA capture bead by covalent linkage. However, non-covalent linkages, such as chelation or antigen-antibody complexes, may also be used to join the oligonucleotide to the bead.

As non-limiting examples, oligonucleotides can be employed which specifically hybridize to unique sequences at the end of the DNA fragment, such as the overlapping end from a restriction enzyme site or the "sticky ends" of cloning vectors, but blunt-end linkers can also be used. These methods are described in detail in U.S. Pat. No. 5,674,743. It is preferred that the beads will continue to bind the immobilized oligonucleotide throughout the steps in the methods of the invention.

Each capture bead is preferably designed to have a plurality of oligonucleotides that recognize (i.e., are complementary to) a portion of the nucleic template, and the amplification copies of this template. It is preferred that any one capture bead contain only one unique nucleic acid species.

The beads used herein may be of any convenient size and fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase supports known to those of skill in the art. In preferred embodiments, the capture beads are beads approximately 2 to 100 μm in diameter, or 10 to 80 μm in diameter, most preferably 20 to 40 μm in diameter. In a preferred embodiment, the capture beads are Sepharose beads.

Emulsification

Capture beads with or without attached nucleic acid template may be suspended in a heat stable water-in-oil emulsion. Furthermore, the size of the microreactors may be adjusted by varying the flow rate and speed of the components. Additionally droplet size can also be varied by changing the viscosity of the emulsion oil, and also by the using different orifice sizes in the cross-flow emulsion generating part.

Various emulsions that are suitable for biologic reactions are referred to in Griffiths and Tawfik, EMBO, 22, pp. 24-35 (2003); Ghadessy et al., Proc. Natl. Acad. Sci. USA 98, pp.

4552-4557 (2001); U.S. Pat. No. 6,489,103 and WO 02/22869, each fully incorporated herein by reference. It is noted that Griffiths et al., (U.S. Pat. No. 6,489,103 and WO 99/02671) refers to a method for in vitro sorting of one or more genetic elements encoding a gene products having a desired activity. This method involves compartmentalizing a gene, expressing the gene, and sorting the compartmentalized gene based on the expressed product. In contrast to the present invention, the microencapsulated sorting method of Griffith is not suitable for parallel analysis of multiple microcapsules/microreactors because their nucleic acid product is not anchored and cannot be anchored. Since the nucleic acids of Griffiths are not anchored, they would be mixed together during demulsification.

The emulsion is preferably generated by adding beads to an amplification solution. As used herein, the term "amplification solution" means the sufficient mixture of reagents that is necessary to perform amplification of template DNA. One example of an amplification solution, a PCR amplification solution, is provided in the examples below. It will be appreciated that various modifications may be made to the amplification solution based on the type of amplification being performed and whether the template DNA is attached to the beads or provided in solution. The oil used may be supplemented with one or more biocompatible emulsion stabilizers including Agrimer AL22 and other recognized and commercially available suitable stabilizers.

In preferred aspects, the emulsion is heat stable to allow thermal processing/cycling, e.g., to at least 94° C., at least 95° C., or at least 96° C. Preferably, the droplets formed range in size from about 5 microns to 500 microns, more preferably, from about 50 to 300 microns, and most preferably, from about 100 to 150 microns. Advantageously, cross-flow emulsion generation allows for control of the droplet formation, and uniformity of droplet size.

The microreactors should be sufficiently large to encompass sufficient amplification reagents for the degree of amplification required. However, the microreactors should be sufficiently small so that a sufficient number of microreactors, up to about 20,000,000 or more, each containing effectively a single member of a DNA library, can be supplied from a small number of conventionally available syringes that can fit together on a syringe pump. Notably, the use of microreactors allows amplification of complex mixtures of templates (e.g., genomic DNA samples or whole cell RNA) without intermixing of sequences, or domination by one or more templates (e.g., PCR selection bias; see, Wagner et al., 1994, Suzuki and Giovannoni, 1996; Chandler et al., 1997, Polz and Cavanaugh, 1998).

With the limitations described above, the optimal size of a microreactor may be on average 100 to 200 microns in diameter. Microreactors of this size would allow amplification of a DNA library comprising about 18,000,000 members supplied to the emulsion generator in a volume of 9 mls contained in three 3 ml syringes.

Amplification

After encapsulation of the bead and PCR solution and template DNA in the micro-reactor, the template nucleic acid may be amplified, while attached (preferably) or unattached to beads, by any suitable method of amplification including transcription-based amplification systems (Kwoh D. et al., Proc. Natl. Acad Sci. (U.S.A.) 86:1173 (1989); Gingeras T. R. et al., WO 88/10315; Davey, C. et al., EP Publication No. 329,822; Miller, H. I. et al., WO 89/06700), "RACE" (Frohman, M. A., In: PCR Protocols: A Guide to Methods and Applications, Academic Press, NY (1990)) and one-sided PCR (Ohara, O. et al., Proc. Natl. Acad. Sci. (U.S.A.) 86.5673-5677 (1989)). Still other methods such as di-oligonucleotide amplification, isothermal amplification (Walker, G. T. et al., Proc. Natl. Acad. Sci. (U.S.A.) 89:392-396 (1992)), Nucleic Acid Sequence Based Amplification (NASBA; see, e.g., Deiman B et al., 2002, Mol Biotechnol. 20(2):163-79), whole-genome amplification (see, e.g., Hawkins T L et al., 2002, Curr Opin Biotechnol. 13(1):65-7), strand-displacement amplification (see, e.g., Andras S C, 2001, Mol Biotechnol. 19(1):29-44), rolling circle amplification (reviewed in U.S. Pat. No. 5,714,320), and other well known techniques may be used in the present invention.

In a preferred embodiment, DNA amplification is performed by PCR. PCR according to the present invention may be performed by encapsulating the target nucleic acid with a PCR solution comprising all the necessary reagents for PCR. Then, PCR may be accomplished by exposing the emulsion to any suitable thermal processing regimen known in the art. In a preferred embodiment, 30 to 60 cycles, and preferably about 60 cycles, of amplification are performed. It may be desirable, but not necessary, that following the amplification procedure, there may be one or more hybridization and extension cycles, which comprise a similar melting time but a longer extension time, following the cycles of amplification. Routinely, the template DNA is amplified until typically at least two million to fifty million copies, preferably about ten million to thirty million copies of the template DNA are immobilized on each bead.

In some embodiments, the method of the invention employs continuous flow PCR to amplify the nucleic acid template. Various methods of continuous flow PCR have been reported in, e.g., Park et al., 2003, Anal. Chem. 75:6029-6033; Curcio and Roeraade, 2003, Anal. Chem. 75:1-7; Chiou et al., 2001, Anal. Chem. 73:2018-2021; U.S. Pat. No. 6,207,031; U.S. App. Pub. 2001/0020588; Lagally et al., 2001, Anal. Chem. 73:565-570; U.S. Pat. Nos. 6,361,671, 6,284,525, 6,132,580, 6,261,431, 6,045,676, 6,143,152, 5,939,312; U.S. App. Pub. 2002/0068357; Schneegas et al., 2001, Lab on a Chip 1:42-49; Kopp et al., 1998, Science 280:1046-1049; Nakano et al., 1994, Biosci. Biotech. Biochem. 58:349-352; and Larzul in U.S. Pat. No. 5,176,203, all of which are incorporated herein by reference. Advantageously, continuous flow PCR greatly reduces sample handling and reaction times, while it increases amplification specificity. However, previous flow systems utilized serial slugs, i.e., slugs of reagent that completely fill the diameter of the flow tube, that are separated by similar full slugs of air and oil. In contrast, embodiments of the present invention are directed to the a water-in-oil emulsion used in conjunction with a continuous flow PCR. The water-in-oil emulsion comprises microreactors, allowing clonal amplification of a large population of nucleic acids. The microreactors are about 10 to 50 times smaller than the diameter of the flow tube so that a very large number of them are present in the flow stream. For example, a 2 mm diameter flow tube can carry 2,000 microreactors per cm of length.

The continuous flow PCR methods of the invention can be used to amplify the sequences of an entire genome or transcriptome on a single instrument in less than half the time required for traditional thermal processing. Continuous flow of the emulsion across a solid state heat transfer element permits efficient and rapid (e.g., 60 second) reaction cycle. A 60 cycle amplification for example, would take 1 hour. In various embodiments, the nucleic acid template can be diluted to obtain effectively one copy of delivered template per microreactor, and a final yield of 1,000,000 to 10,000,000 template copies per bead. As examples, the continuous flow methods of the invention can be used with thermal amplification reactions (e.g., PCR) or isothermal reactions (e.g., rolling circle amplification, whole genome amplification, NASBA, strand displacement amplification, and the like).

Amplification Systems

In one aspect, the method of the invention is performed using a system for continuous flow amplification, e.g., continuous flow PCR amplification. This system includes a means for forming an emulsion of an amplification reaction mixture in a stabilized biocompatible oil.

FIG. 1 illustrates a general block diagram of an emulsification system 200, as well as a thermal processor 112 and bead filtering device 114, according to one embodiment of the present invention. As shown, an emulsion oil 102 is pumped via pump 104 into a cross-flow emulsifier 106. The emulsifier emulsifies a PCR reaction mixture (having a plurality of beads) 108, which is supplied to the emulsifier via a pump 110, creating a plurality of microreactors in the emulsion oil flow. Each microreactor preferably includes on average a single bead and an effective single species nucleic acid template.

The plurality of microreactors may then be thermally processed via a thermal processor 112 to amplify the DNA template. After amplification, the beads (each containing the amplified nucleic acid), may be filtered out of the emulsion flow via a bead filter 314, and thereafter processed for subsequent sequencing.

Figure 2:
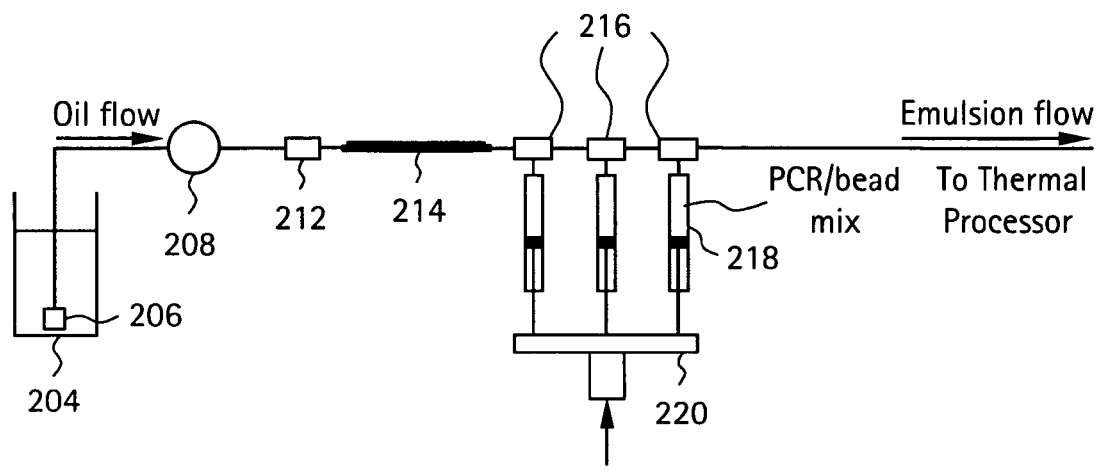
FIG. 2 is a schematic of a linear emulsification system according to an embodiment of the present invention for creating an emulsion flow.

FIG. 2 illustrates a schematic diagram of an exemplary emulsification system 200. As shown, an emulsion oil 202 from an emulsion oil supply 204, via filter 206, is pumped via pump 208 to a cross-flow emulsifier 210. The system may be controlled by a microprocessor based controller (not shown), which may be a personal computer (PC), or other controller (e.g., analog) controller device. Accordingly, the controller may monitor the pressure of the emulsion oil flow via pressure sensor 212, so that the flow rate of the oil may be regulated, and the general status of the system determined (e.g., pump failures, leaks). The pump is preferably precisely controlled (e.g., electronically) to maintain an exact and consistent speed (e.g., from 1-10 mls/min, and preferably about 3 mls/min). A pressure dampening tube 214 may be used to attenuate pressure fluctuations in the oil caused by the pump, prior to the first cross-flow emulsifier.

Figure 3:
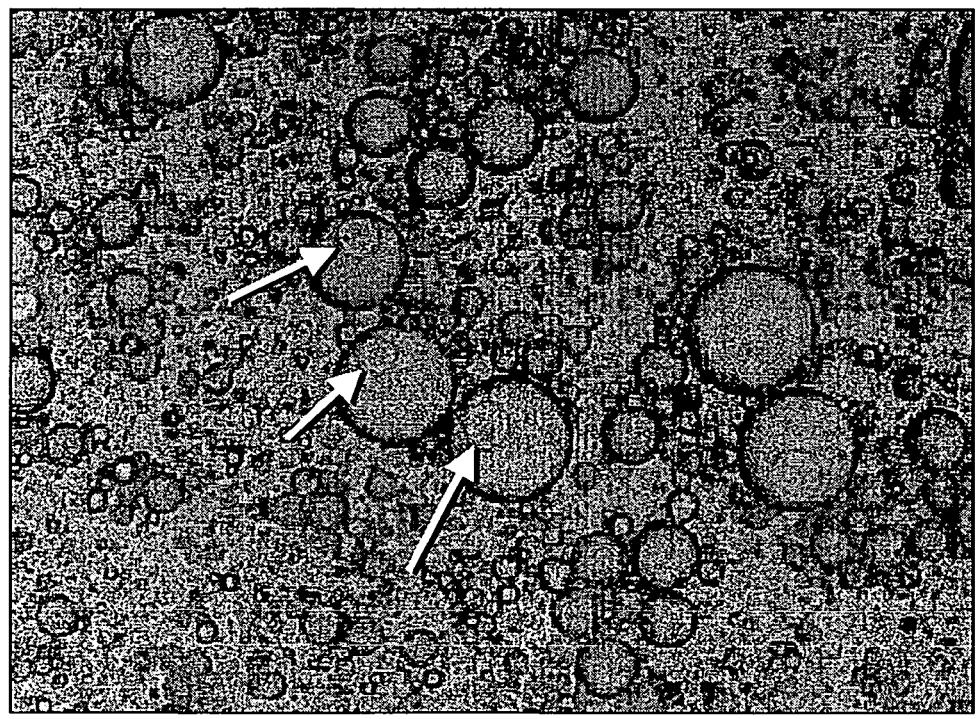
FIG. 3 illustrates a depiction of beads (see arrows) suspended in individual microreactors according to some embodiments of the invention.

The emulsion oil is supplied to the cross-flow emulsifier 210 (see also 106, FIG. 1). In this particular embodiment, the emulsion oil is flowed through multiple (in this case, three) injection/mixing tees 216 (although a single injection tee or any other number may also be used). Each tee receives a PCR/bead mixture from a corresponding syringe 218. A syringe pump 220 may be used to drive the plunger of each syringe at a controlled rate to force the PCR mixture from the syringe into the respective tee. A tee enables a respective syringe to create a plurality of microreactors (each preferably containing a single bead on average and an effective single nucleic acid template) in the emulsion oil. Thereafter, the emulsion flow (with microreactors) is sent to a thermal processor so that the nucleic acid template supplied in each microreactor may be amplified for nucleic acid amplification. FIG. 3 illustrates an example of beads (see arrows) suspended in individual microreactors.

Figure 4:
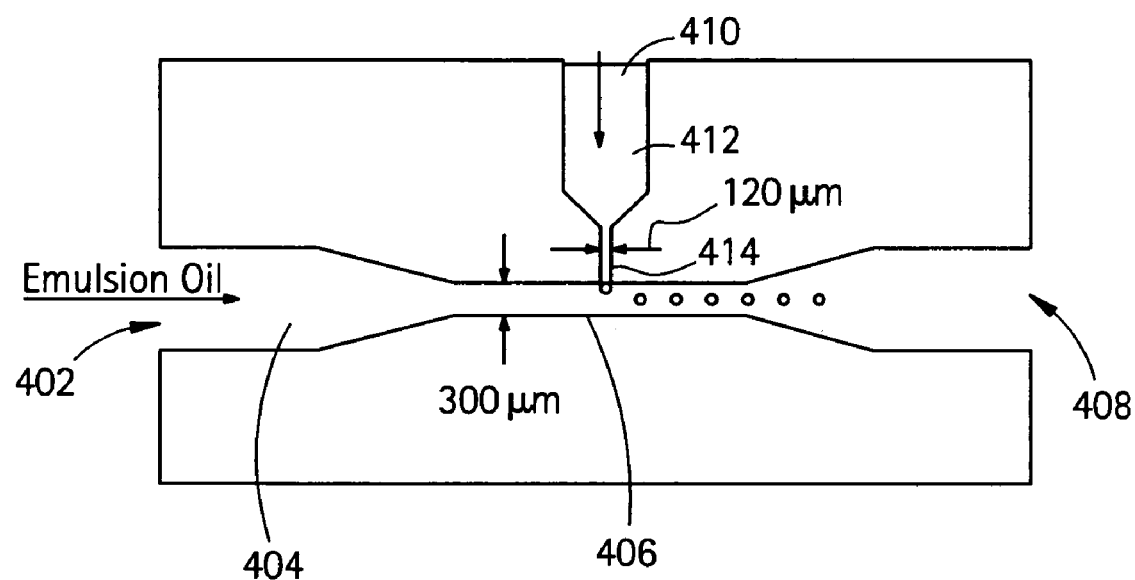
FIG. 4 is a schematic of a linear emulsifier apparatus according to an embodiment of the present invention.

FIG. 4 illustrates a general schematic of an injection tee emulsifier 400 that may be used with some of the embodiments of the present invention, which allow, for example, droplet generation rates on the order of 500 to 1000 per second or more, and FIGS. 5A-5F illustrate various views of particular injection tee emulsifiers according to some embodiments of the invention.

As shown in FIG. 4, the emulsifier may include a first inlet 402 of a first conduit 404 for receiving an emulsion oil, a narrowed diameter area 406 provided along the first conduit and an outlet 408 of the first conduit. Preferably, the first conduit is provided in a horizontal position thereby establishing a cross-flow of emulsion oil through the narrowed area. Moreover, a diameter of the narrowed area is preferably between 100 μm and 600 μm, more preferably between 200 μm and 400 μm, and most preferably approximately 300 μm.

The emulsifier 400 also includes a second inlet 410 of a second conduit 412 for directing amplification reaction/bead mixture into the apparatus. A tubular orifice 414 is provided at a terminus of the second conduit, and is open to the narrowed area 406 of the first conduit. The orifice preferably includes a diameter of between about 10 um to about 200 μm, and more preferably between 75 μm and 150 μm, and most preferably about 120 μm. Preferably, the second inlet, conduit and orifice are provided in a vertical arrangement relative to the preferred horizontal arrangement of the first conduit (i.e., the first conduit and second conduit/orifice may be orthogonal to one another), although any orientation can work. The orifice enables a plurality of amplification reaction mixture droplets (i.e., microreactors), to be created as the reaction mixture enters the oil flow. A plurality of such microreactors each preferably include on average a single bead and an effective single nucleic acid template.

Figure 5A:
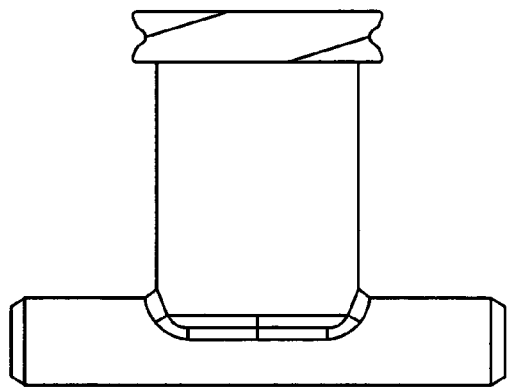
FIG. 5A is front view of a mixing Tee for a linear emulsification apparatus according to an embodiment of the present invention.
Figure 5B:
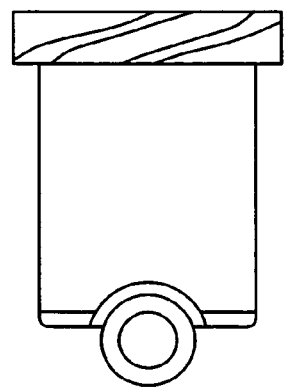
FIG. 5B is a side view of the mixing Tee of FIG. 5A.
Figure 5C:
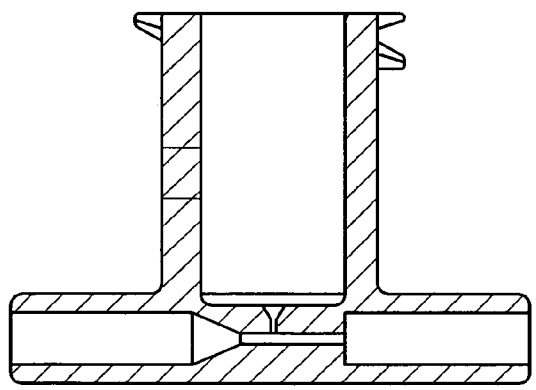
FIG. 5C is a cross-sectional view of the mixing Tee of FIG. 5A.
Figure 5D:
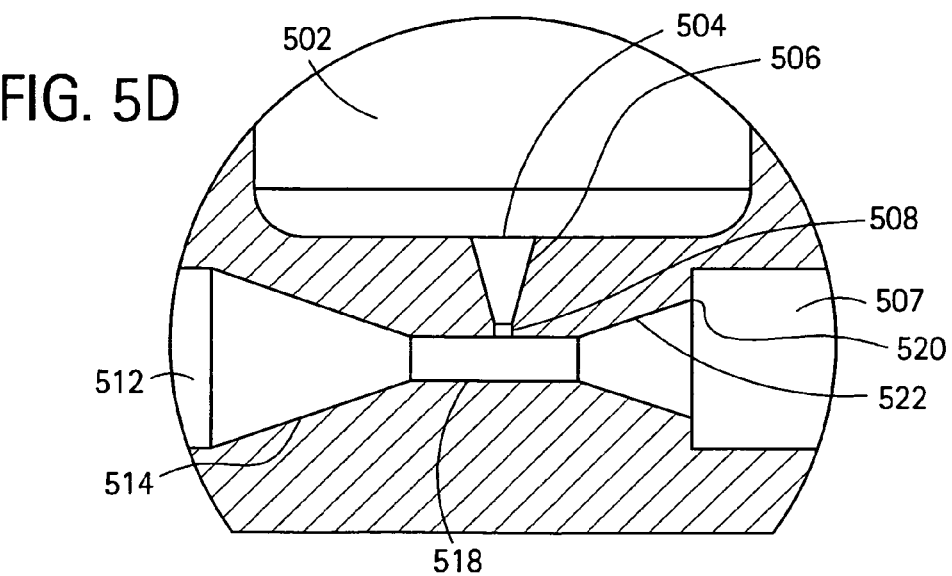
FIG. 5D is an enlarged cross-section of the detail of the nozzle area of the mixing Tee of FIG. 5A.
Figure 5E:
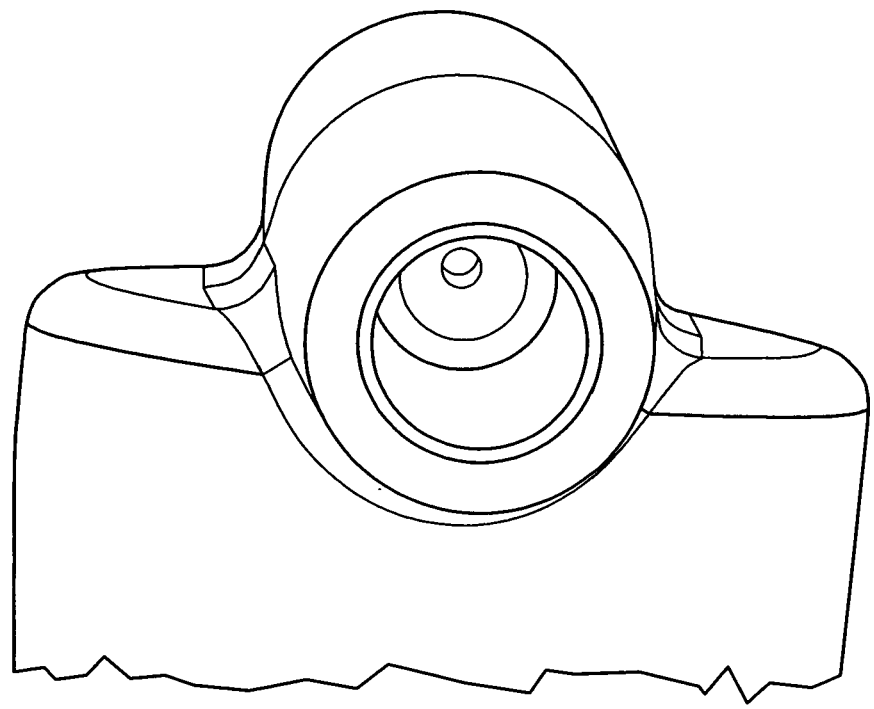
FIG. 5E is a close-up, perspective view of mixing area of the mixing Tee of FIG. 5A.
Figure 5F:
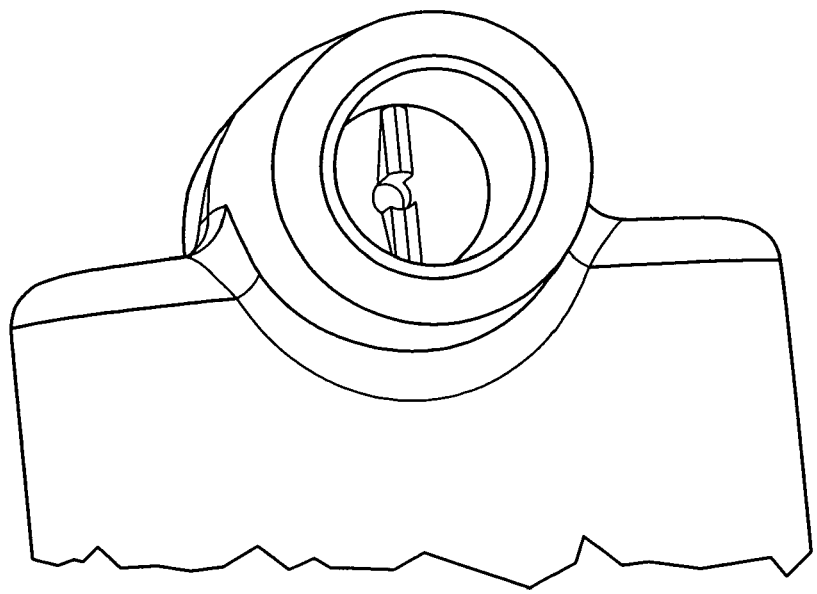
FIG. 5F is a close-up, perspective view of an alternative design of the mixing area of the Tee of FIG. 5A.

With reference to FIG. 5D, a particular injection tee includes a syringe exit area 502d, an aqueous phase (PCR solution) inlet area 504d, a tapered area of injection port 506d, a straight area of injection port 508d, an emulsion exit 510d, an emulsion oil inlet 512d, a tapered oil acceleration area 514d (i.e., nozzle), a constant speed, high velocity (narrowed) area 516d, a partial diffusion area 518d and a diffuser step 520d.

Accordingly, when the emulsion oil enters a respective injection tee, it enters a progressively narrower region, and is thus accelerated to a higher velocity (e.g., 30 times its initial velocity). The PCR/bead solution (i.e., an aqueous phase material) is then injected at preferably a constant and controlled rate, preferably between about 5 μl-100 μl per minute, and preferably about 20 μl/minute. One of skill in the art will appreciate that other relative flowrates for the two component fluid sources may be used in accordance, for example, with the specifications of a thermal processing device for PCR amplification.

The shearing force of the high velocity oil breaks off the PCR/bead stream into individual droplets as it is being injected, each preferably including a single bead. As the newly formed droplets move downstream, the velocity of the flow may be gradually reduced in a diffuser area (see partial diffuser area 522, FIG. 5D). After the partial diffuser, the flow encounters an abrupt step (520, FIG. 5D), which causes the droplets to break away from the wall and enter the central area of the flow stream. The flow then exits the injection tee with the droplets evenly distributed throughout the flow.

The examples of injection tees illustrated in FIGS. 5A-5D may be made to fit a disposable syringe, and may be manufactured via plastic injection molding. In some embodiments of the invention, the selection of an appropriate plastic material is critical to impart the desired function of the mixing tee. Specifically, the surface of the material must preferentially wet with oil rather than water. If this is not the case, the incoming stream of aqueous material will flow along the inside wall of the high-velocity area of the tee in a continuous stream, rather than be sheared into the desired sized droplets. Polypropylene, for example, is a plastic material that has meets these requirements. An additional requirement for the tee is that the internal geometry must cause the newly formed emulsion droplets to leave the wall of the oil conduit (where they are formed) and migrate to the central area of the flow stream. If this does not occur, the droplets will be too close together and the risk of collisions and coalescence will be high. To that end, present examples of the injection tees include internal geometry features which induce the emulsion droplets to separate from walls and flow into the central area of the conduit.

The PCR/bead mixture is provided to the injection tee using a syringe pump, an example of which is illustrated in FIGS. 6A-6E. As illustrated generally in FIGS. 6A-6C, the syringe pump 600 generally includes one or more syringes 602, a syringe holder block 604, guide rods 606, a drive screw 608, a motor 610, a base 612, a slider assembly 614 and a pivoting door assembly (which may be spring-loaded) 616. The slider assembly is driven by the drive screw, which in turn simultaneously drives each plunger of each syringe into the syringe body to drive out the contents of the syringe. The motor, which may be a stepper motor, turns a drive pulley 618, which drives a main drive pulley 620 via belt 622, which rotates the drive screw to move the slider assembly (to move the syringe plungers).

Figure 6A:
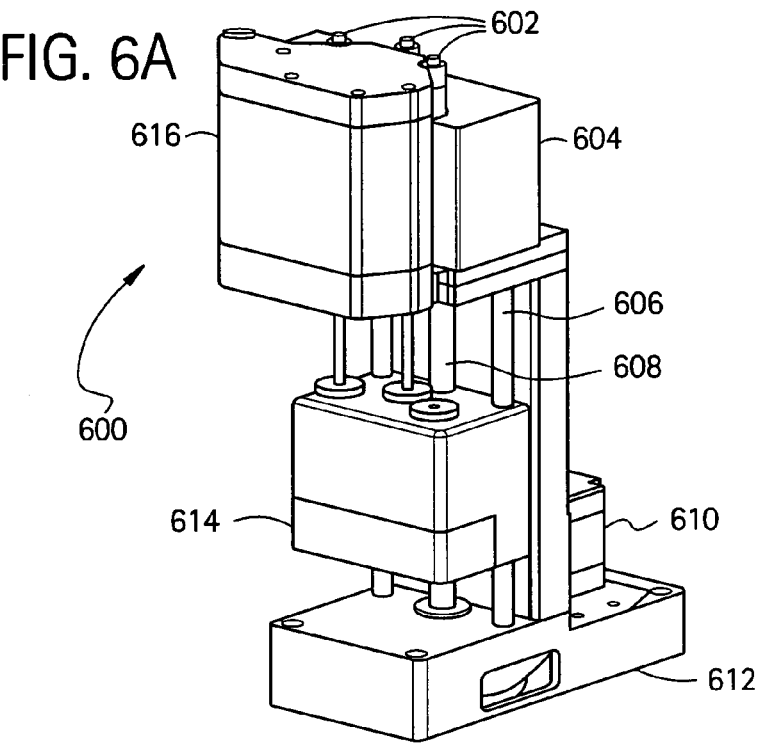
FIG. 6A is a first, side-perspective view of a syringe pump assembly according to one embodiment of the present invention.
Figure 6B:
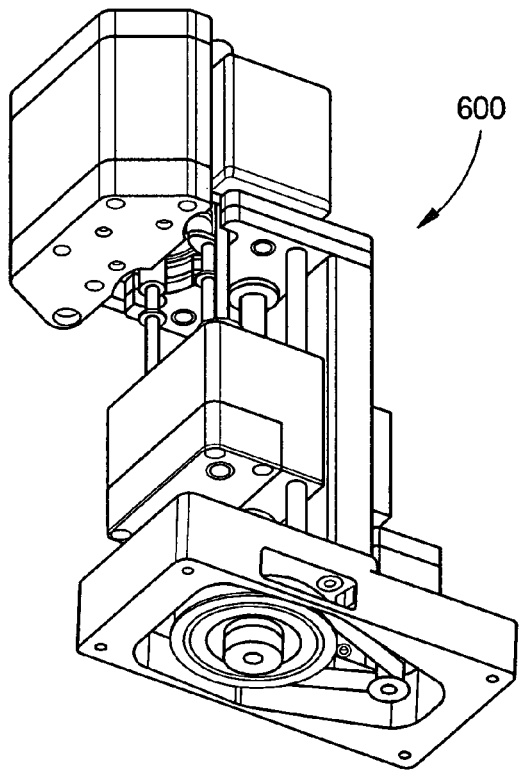
FIG. 6B is bottom-perspective view of the syringe pump assembly of FIG. 6A.
Figure 6C:
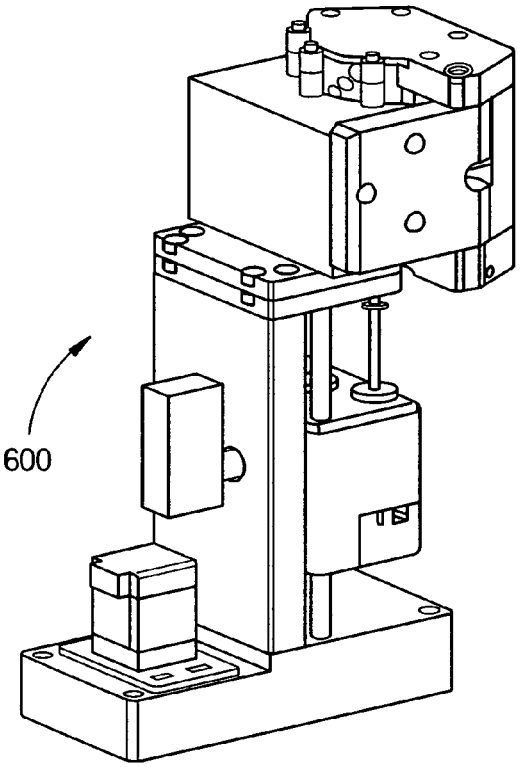
FIG. 6C is a backside-perspective view of the syringe pump assembly of FIG. 6A.
Figure 6D:
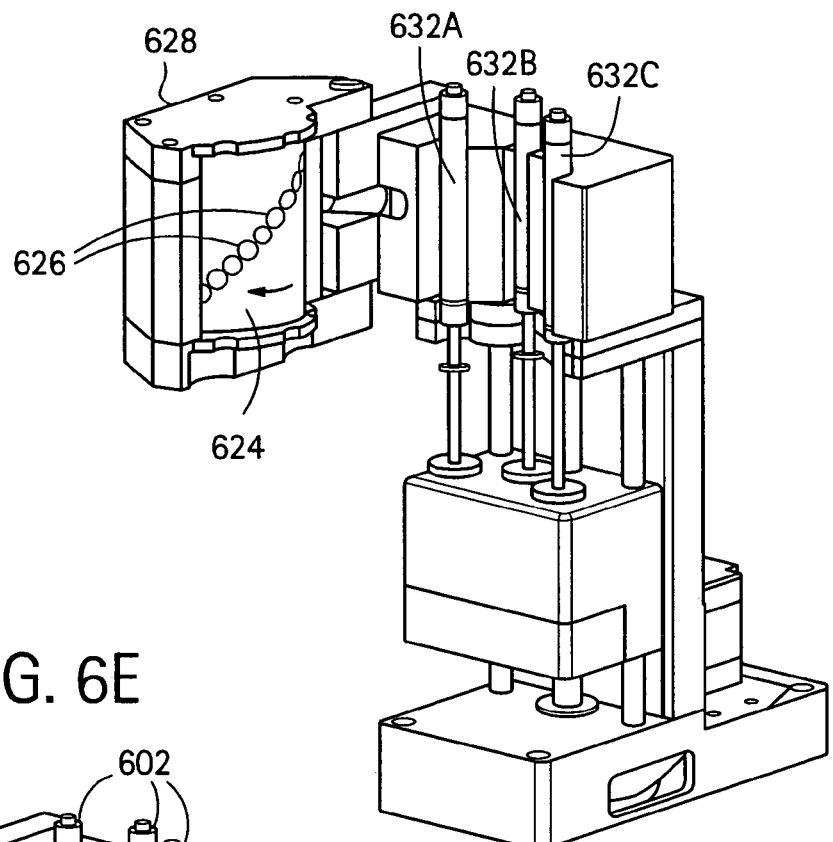
FIG. 6D is a second, side-perspective view of the syringe pump assembly of FIG. 6A.

To insure the beads are evenly distributed throughout the solution within each syringe a mixing mechanism may also be included with the syringe pump. As shown in FIG. 6D, a rotating element 624 (drum) may be included (in this case, positioned in the pivoting door assembly) which includes a helical line of magnets 626 along a portion of the drum surface positioned adjacent each syringe body. In an operating position, the rotating element rotates so that the helical line of magnets come into close proximity to the bodies of the syringes as they pass by. An electric motor (not shown) with a gear reduction unit may be used to power the rotating element and may be mounted inside the rotating element (being secured to the door frame). The plurality of magnets may also be represented by a single, helically wound magnet-strip (or other formed magnet, which is helically arranged around the rotating element), but a plurality of individual magnets is preferred.

The magnets 626 in the rotating element are preferably oriented so that the fields are directed out radially from the rotating element. Preferably, a majority (and most preferably, all) of the magnets have the same polarity orientation.

As the helically mounted line of magnets 626 pass by the body of each syringe, a magnetic ball 632a, 632b, 632c, included inside each syringe body is moved from its lowest position adjacent the plunger 634 toward a higher position, which may be adjacent the nozzle area 636, successively, higher and higher by each magnet. The ball is released once the highest magnet in the helical series moves away from the syringe body and then drops to the bottom (i.e., adjacent the plunger) of the syringe. This motion of the mixing ball will occur regardless of where the syringe plunger is located. The frequency and velocity of the mixing ball may be controlled by the rotational speed of the rotating element. Preferably, as the syringe becomes less full, the ball moves more quickly to accomplish the same mixing effect. More than one helical pattern of magnets may be used to allow different mixing rates and displacements as the plunger moves through different areas of the syringe. For example, it is desirable that the mixing action does not disturb the injection tee, so one series of magnets may start at the lowest point of the plunger and only go part way up the syringe body, while a second line of magnets may start at the middle and continue to the top. The lower magnets would work when the plunger is low, and the upper portion of the magnets would only work when the plunger is in the upper range of its motion. Another variation is for the helix of magnets to go both upward and downward, thereby controlling the motion throughout and allowing the mechanism to work in any orientation.

Figure 6E:
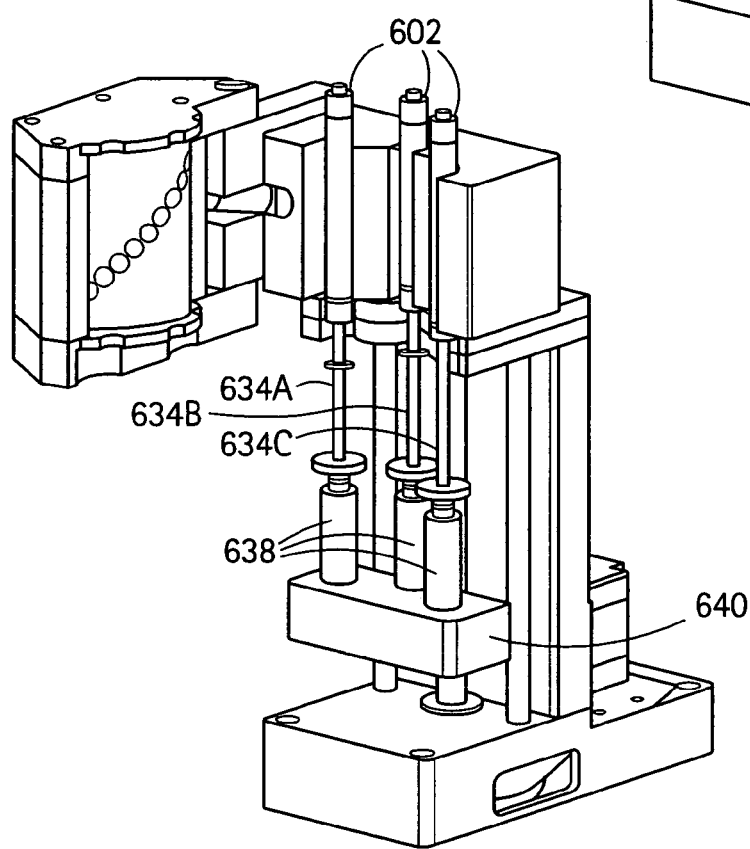
FIG. 6E is third, side-perspective view of the syringe pump assembly of FIG. 6A.

To insure the beads do not clog the nozzle in the mixing tee, some embodiments of the present invention make use of a anti-clogging device. More particularly, some embodiments of the present include a sonic (vibratory), anti-clogging mechanism (FIG. 6E) for reliably feeding solid particles at high concentrations through the nozzle of the mixing tee. As shown in FIGS. 6E, each plunger 632a, 632b, 632c may be fitted with a piezo-electric actuator 638 (i.e., sonic actuator), which is provided in the slider assembly of the syringe pump. The piezo-electric actuator(s) are driven electronically at a desired frequency (between about 50 Hz and 1000 Hz, and preferably about 300 Hz) and displacement (between about 1 $\mu l$-100$\mu$, and preferably about 15$\mu$) to effectively keep the particles in the nozzle in constant motion to prevent clumping & clogging of the beads in the nozzle area. Electromagnetic actuators can also be used to create & impart the energy to the syringes.

Without the use of the sonic actuators according to the present invention, large amounts of viscosity enhancers and surfactants would be required to prevent particles from clogging the nozzles, and such a system would still only be marginally reliable. Another important function of the vibratory mechanical excitation of the syringe plungers is that it prevents the rubber syringe plungers from sticking to the internal body of the syringe. If this happens, a slip-stick intermittent motion of the syringe plunger will occur, causing the bead/PCR solution to be fed at a variable rate, causing droplet size control to be impossible.

The flow exiting from the emulsifier, via a conduit (for example) may be then run through a thermal processing device, which exposes the continuous flow to alternate zones of a higher temperature and lower temperature (e.g., a heating zone and a cooling zone) for PCR amplification. Examples of such thermal processing devices are illustrated in FIGS. 7A-7B and FIGS. 8A-8C. Some embodiments of the thermal processors according to the present invention allow for rapid, simultaneous and separate PCR amplification of millions of DNA fragments, resulting in clonal solid phase products. Over 12 million (for example) separate DNA fragments can be separately amplified in one batch.

Figure 7A:
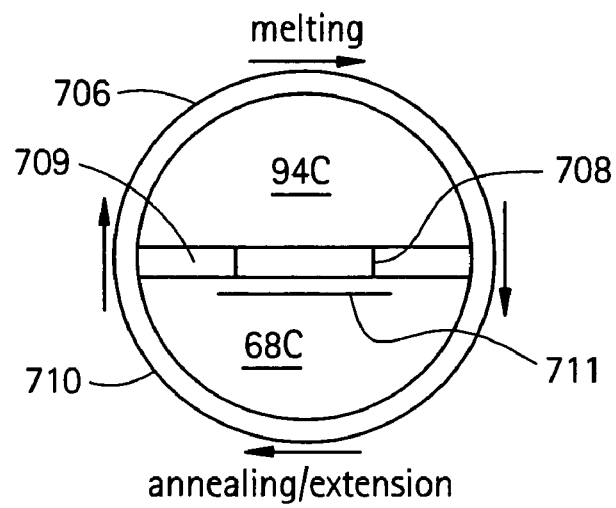
FIG. 7A is a schematic of a circular thermal processing system.
Figure 7B:
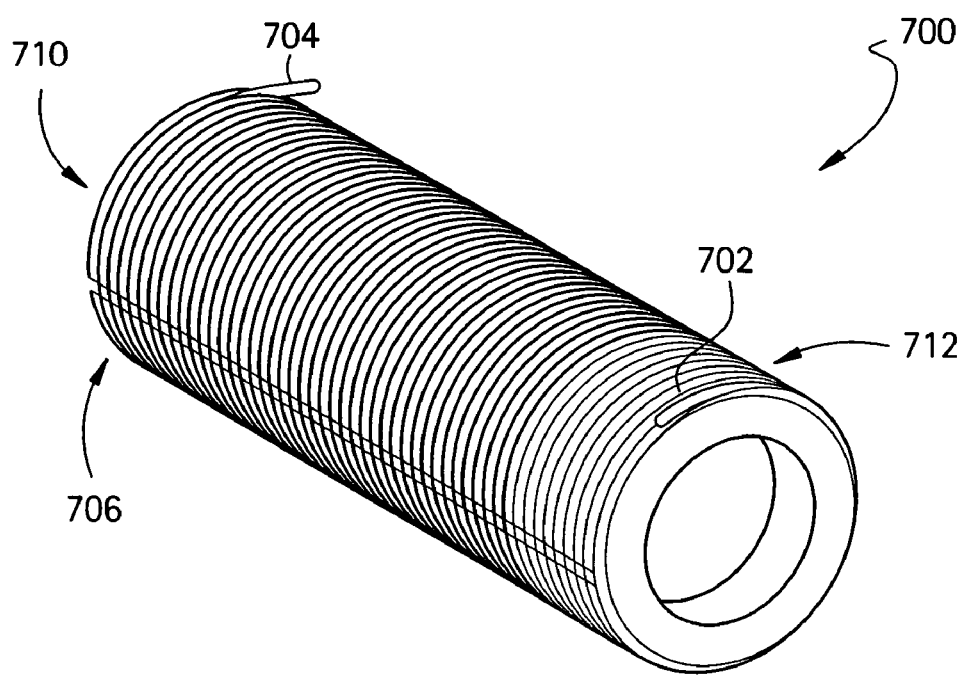
FIG. 7B is a perspective view of the circular thermal processing system of FIG. 8A.
Figure 8A:
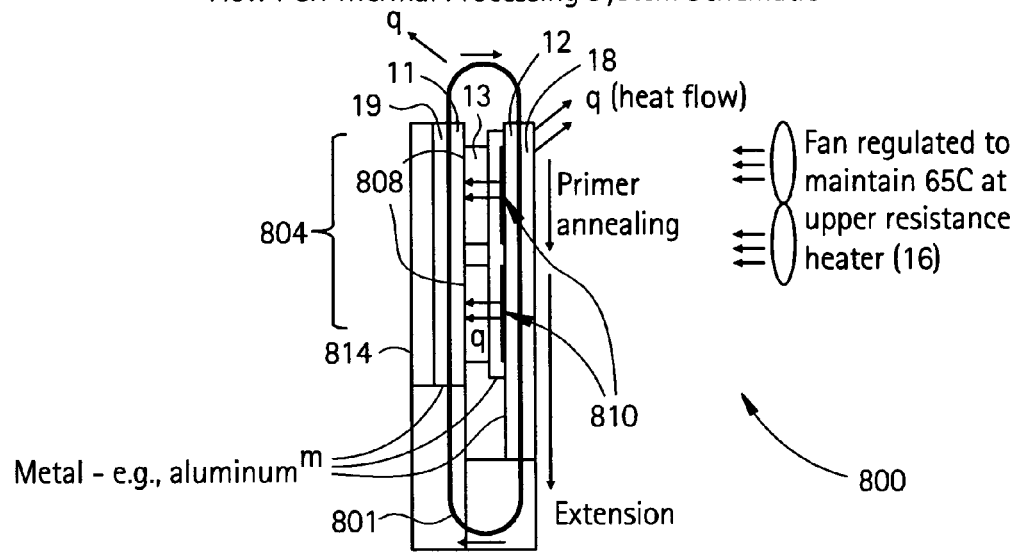
FIG. 8A is a schematic of another example of a continuous flow thermal processing/cycling system according to another embodiment of the invention.
Figure 8B:
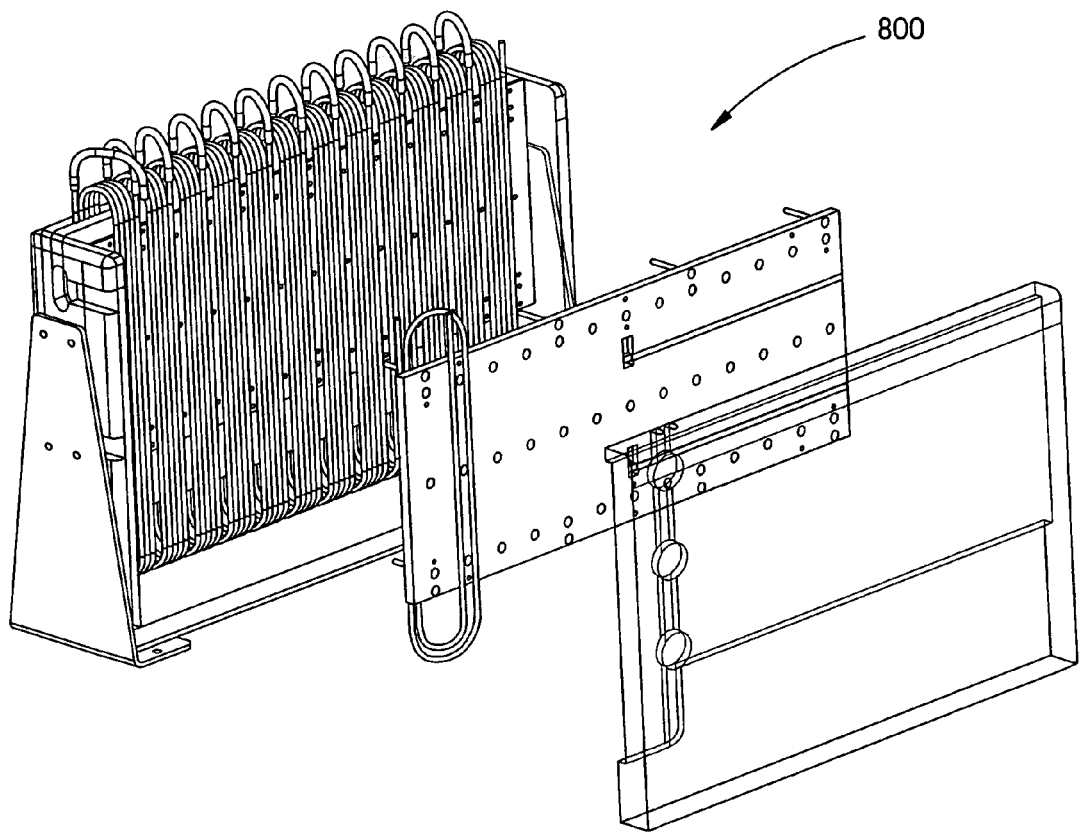
FIG. 8B is an exploded-perspective view of the thermal processing system of FIG. 7A.
Figure 8C:
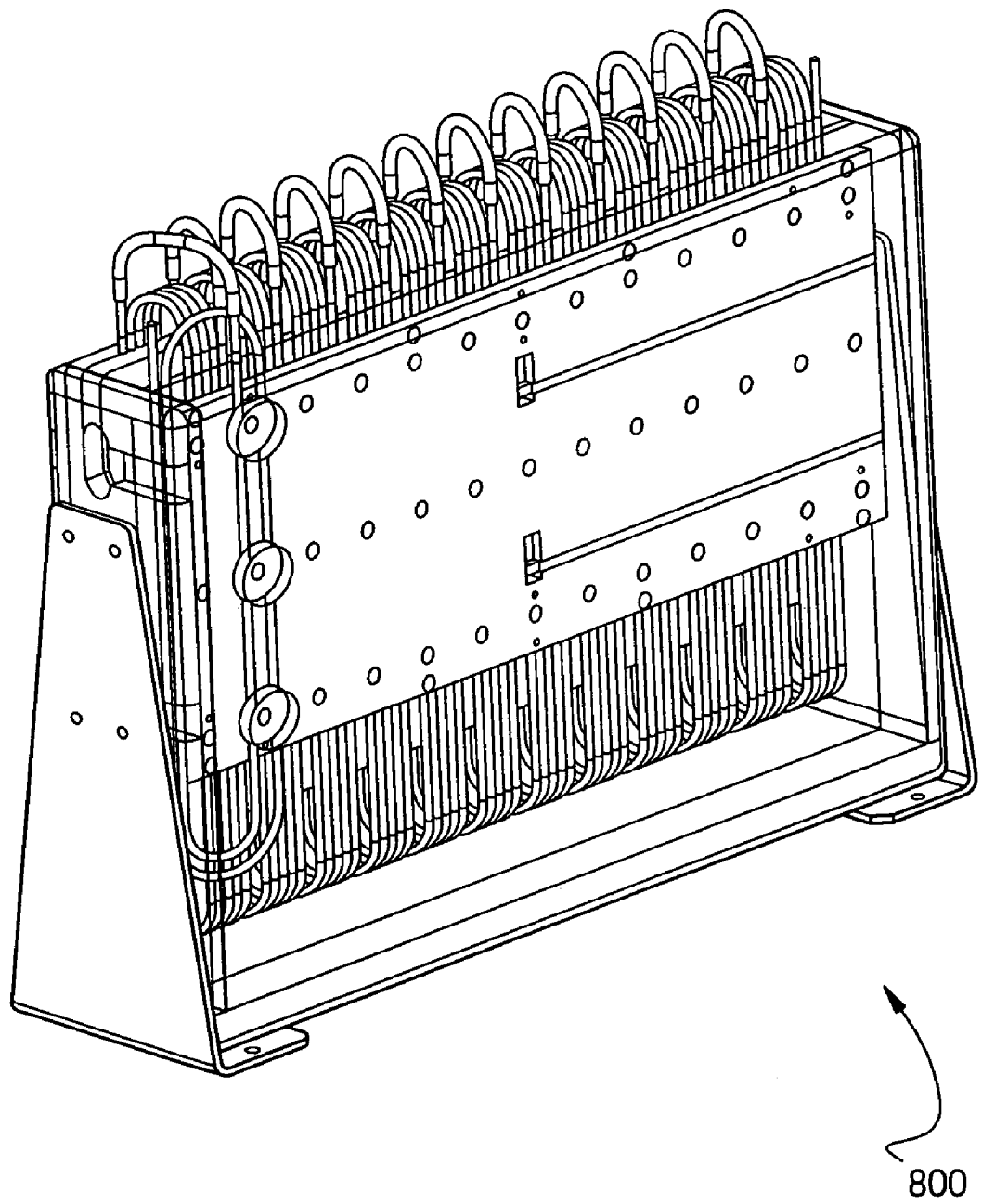
FIG. 8C is an assembled, perspective view of the thermal processing system of FIG. 7B.

For example, a stainless steel conduit, including an inlet 702 and an outlet 704, containing the emulsified flow (e.g., 400 as shown in FIG. 4) may be helically wound around a mandrel type thermal processing device 700 (FIG. 7A-7B). One side or portion of the mandrel comprises a first temperature zone 706 which may include a heater or heat transfer element 708, surrounded by an insulation material 709 (for example) and a second side or portion of the mandrel comprises a second temperature zone 710 which includes a temperature lower than the temperature of the first temperature zone. The second temperature zone may include a cooling element (e.g., water jacket, air circulation fan, and the like) to cool the continuous flow, but may also include a resistance heater 711 (for example) to maintain a certain predetermined temperature. A preheating zone 712 may also be included, prior to the flow reaching the first temperature zone.

Alternatively, the second temperature zone may also include a heating element, since the zone typically, for PCR amplification, maintains a temperature of between approximately 60-70 degrees C., which is considerable higher than room temperature of 23 degrees C. Such an example is shown in the thermal processor illustrated in FIGS. 8A-8C. If a heat transfer element, such as a thermoelectric device, is used to provide heat to the first temperature zone, the heat will come from the second zone, which must have a heating element to maintain temperature. This is the desirable approach because it generates the least possible amount of waste heat and therefore has the lowest energy consumption and the lowest cooling requirement.

In this example, the thermal processing device 800 allows alternating sections of a conduit 802 to be positioned adjacent opposed (for example) linear first temperature 804 and second temperature 806 zones. One or more thermoelectric heat transfer elements 808 of the thermal processing device may provide heat to the continuous flow along portions of the conduit. Resistance heaters 810 may be positioned adjacent the second temperature zone 806, so that the conduit sections positioned adjacent the second temperature zone is maintained at, for example, between a temperature of, for example, 60-70 degrees C. The second temperature may maintained by both adding heat from the heating elements when required, and also by removing heat in the second zone, using (for example) a fan to move air across the second zone. Another feature that may be included is an exposed area of conduit between the first and second temperature zone, which allows the conduit to be directly cooled by the fan, rather than via the second temperature zone block.

In this example, the resistance heaters may also provide thermal energy for the first temperature zone. Blocks 812 may be used as thermal conductors to conduct heat to and from the various zones and to and from the conduit, and may be fabricated from any material useful for heating, e.g., metal such as aluminum, copper, and the like. The blocks may be designed to be a precise fit around the conduit so that thermal energy may be efficiently transferred between the blocks and the conduit. A thermal grease may be added between these two elements to further improve the thermal conductivity of the interface. Insulation 814 may also be used to help maintain temperature of the high temperature zone, or any other area of the thermal processing device. In one example, the conduit may extend 46 cm for each amplification cycle, for a total of 35 cycles. In another example, the conduit is 67 cm for each cycle, and a total of 60 cycles are used. The conduit is made in groups of five cycles, so that sufficient fasteners may be used to ensure that the blocks are tightly clamped around the conduit. To allow a pre-heating step, an additional length of conduit may be added in the beginning that is exposed only to the high temperature zone. This may be included for the purpose of activating an enzyme required for PCR amplification. Further still, a distal end of the conduit may be adapted to allow for sample collection, e.g., into a bead filtering device or a collection container.

For PCR, the temperature in the first temperature zone of between 90 and 100 degrees C. may be used to melt duplex nucleic acid (e.g., 94° C.), while the 60-70 degrees C. temperature of the second temperature zone is chosen for primer annealing and extension (e.g., 65° C.), for example.

While the delivery of the emulsion components can be accomplished by any manual or automatic delivery means, preferably a pump system is used. As illustrative examples, delivery can be obtained by various pumps, including syringe pumps and mechanical pumps, e.g., HPLC pumps (see, e.g., Gilson, Inc., Middleton, Wis.; ESA, Inc., Chelmsford, Mass.; Jasco Inc, Easton, Md.). The preferred means is a rotary annular gear pump.

Exemplary heating devices for the apparatus include, but are not limited to, cartridge heaters (see, e.g., Omega Engineering, Inc., Stanford, Conn.; Delta-t Max, Greenland N.H.), resistive heaters (see, e.g., Minco Products, Inc., Minneapolis, Minn.), and thermoelectric heaters, including Peltier devices (see, e.g., Ferrotec, Nashua N.H.). In various aspects, the heating devices for the apparatus can be embedded in the heating blocks or mounted on the surface of the blocks. Temperature monitors may also be used with the apparatus, including real-time proportional temperature controllers, PID (proportional, integral, and derivative) digital controllers, in combination with temperature sensing elements such as thermocouples, thermistors, or any other suitable device (see, e.g., Watlow Electric Mfg. Co., St. Louis, Mo.).

The conduit material may be fabricated out of any compatible tubing material for amplification (in particular, thermal amplification), such as stainless steel, Polytetrafluoroethylene (PTFE; e.g., Teflon), and fused silica. Preferably, stainless steel tubing is used for its thermal conductivity and corrosion resistance.

It will be understood that other means for controlling amplification for the apparatus are also possible. For example, fluids can be circulated from constant temperature reservoirs, in particular, hot oil baths (see, e.g., Nakano et al., 1994, Biosci. Biotech. Biochem. 58:349-352), and hot water baths (see, e.g., Curcio and Roaeraade, 2003,Anal. Chem. 75:1-7). In addition, it is possible to perform continuous flow amplification on the surface of a chip (see, e.g., Kopp et al., 1998, Science 280:1046-1049; Schneegas et al., 2001, Lab on a Chip 1:42-49). For example, a silicon or glass chip can be modified to include thin film transducers to heat different sections of the chip to different temperatures. Alternatively, a chip can be placed across a row of heating blocks, where each block is heated to a different temperature. The heated sections of the chips can allow for denaturation (e.g., 95° C.), primer annealing (e.g., 58° C. or 60° C.), and primer extension (e.g., 72° C. or 77° C.) steps in the amplification reaction. In addition, fluid channels may be added to the chip (e.g., by etching, molding, imprinting, or adhesives) to allow for buffer and sample input, temperature cycling, and product output. The buffers and samples can be delivered, for example, by precision syringe pumps, and the amplification products can be collected into microfuge tubes, microwells, or other reservoirs. These methods, however, do not provide for the separate amplification of large numbers (thousands or millions) of different DNA fragment templates, which is the critical advantage of this invention.

Bead Recovery

Following amplification of the nucleic acid template and the attachment of amplification copies to the bead, the beads must be recovered. If a filter element is at the exit of the first conduit, the filter may be removed from the system, and beads may be back-flushed out of the filter using reverse flow. The beads may alternatively be washed & processed while they are still in the filter, by attaching the filter to a syringe with the bead side exposed to the syringe chamber, and pulling and pushing various wash reagents through the filter and in and out of the syringe.

Alternatively, the emulsion exiting the flow system may be collected in a vessel, and subsequently spun in a centrifuge, which will leave the beads at the bottom provided they are denser than the oil. The oil may then be removed from above the beads, and the beads my be recovered from the bottom of the vessel. This procedure may also be used without the centrifuge, if sufficient time is allowed for the beads to settle by gravity.

Purifying the Beads

After PCR amplification, the beads may be isolated from the microreactors and used for sequencing. The sequencing steps are preferably performed on each individual bead. However, this method, while commercially viable and technically feasible, may not be most effective because a portion of the beads will be "negative" beads (i.e., beads without amplified nucleic acid attached). This is because the DNA template material is delivered to the PCR solution or the beads by dilution, and it is inevitable that at least some of the beads do not get a starting copy for amplification. In such cases, an optional process outlined below may be used to remove negative beads prior to distribution onto multiwell (e.g., picoliter) plates.

EXAMPLES

Binding Nucleic Acid Template to Capture Beads

This example describes preparation of a population of beads that preferably have only one unique nucleic acid template attached thereto. Successful clonal amplification depends on the delivery of a controlled number of template species to each bead. Delivery of excess species can result in PCR amplification of a mixed template population, preventing generation of meaningful sequence data while a deficiency of species will result in fewer wells containing template for sequencing. This can reduce the extent of genome coverage provided by the sequencing phase. As a result, it is preferred that the template concentration be accurately determined through replicated quantitation.

Template Quality Control

The success of the Emulsion PCR reaction is related to the quality of the template species. Regardless of the care and detail paid to the amplification phase, poor quality templates will impede successful amplification and the generation of meaningful sequence data. To prevent unnecessary loss of time and money, it is important to check the quality of the template material before initiating the PCR phase of the process. Preferably, the template library should pass two quality control steps before it is used in Emulsion PCR. Its concentration and the distribution of products it contains should be determined. Ideally, the library should appear as a heterogeneous population of fragments with little or no visible adapter dimers (e.g., ~90 bases). Also, amplification with PCR primers should result in a product smear ranging, for example, from 300 to 500 bp. Absence of amplification product may reflect failure to properly ligate the adaptors to the template, while the presence of a single band of any size may reflect contamination of the template.

Continuous Flow PCR Amplification

A linear emulsifier included an internal diameter of 300 µm for an oil passage and an internal diameter of 120 µm for the bead/PCR solution outlet (see FIG. 4). The emulsion oil flow rate was set at 2 ml/min, while the PCR solution flow rate was set at 5 µl/min . The droplet (microreactor) size range was 80 µm to 120 µm (270 pl to 900 pl). Droplets were generated at a rate of 55/sec to 180/sec. Bead size was 25 µm to 30 µm, while bead density was 1 bead/nl. The flow tube internal diameter was 2.4 mm. The length of tube for one cycle was 46 cm. Each PCR cycle was timed at 64 sec, which included 35 cycles plus a pre-heat step taking 2 min. The total time for the PCR reaction was 39 minutes.

Solution Phase Reaction Mix:
  1× Hi Fl Buffer
  1 mM dNTPs
  2.5 mM MgSO4
  1 uM forward Primer (MMP 1a)
  1 uM Reverse Primer (MMP 1b)
  0.01% tween-80
  0.1% BSA
  0.15 U/ul Hi Fi Taq Added 3 and 30 Copies of TF7 per nl PCR Mix For Bead experiment used same reaction mix only added 0.333% 4M weight PEO and added 3,600 copeis/nl of TF7 into the solution. Added beads at 1 bead/nl.

| Copy per nl | Amplification Factor |
|---|---|
| 3 | 53 M |
| 30 | 7.6 M |
| 3600 (+beads) | 9,600 |

Pyrosequencing of Beads from Reaction Showed Clear TF7 Sequence.

The total amplification obtained was 50,000,000×, corresponding to 1.66× amplification per PCR cycle.

Another Example of Emulsion Flow PCR

The PCR amplification mixture used contained 1× High Fidelity Buffer (60 mM Tris-SO4 pH 8.9, 18 mM Ammonium Sulfate, (Invitrogen)), 1 mM dNTPs (Pierce), 0.625 mM forward primer, 0.078 mM reverse primer (IDT), 0.25% agrimer AL10-LC (ISP Technologies), 5% PEG-8000 (Acros), 0.02% BSA (Sigma), 0.003 U/ul inorganic pyrophosphotase (NEB), 0.15 U/ul Platinum High Fidelity Taq (Invitrogen).

The library of interest, *E. coli*, was added in three replicates to 1.8 million capture beads in a minimal volume and resuspended by vortexing. This mixture was then added to 900 µl of the PCR mixture. This solution was then loaded into a 1 ml syringe that contained an 4.1 mm plastic coated magnetic mixing ball. Three identical syringes were then loaded in series onto the "Flow PCR Unit".

The emulsion flow PCR system included an internal diameter of 300 µm for an oil passage and an internal diameter of 120 µm for the bead/PCR solution outlet (see FIG. 4). The emulsion oil flow rate was set at 2.4 ml/min, while the PCR solution flow rate was set at 15 µl/min per syringe. Three syringes were used. The droplet (microreactor) size range was 80 µlm to 120 µm (270 pl to 900 pl). Droplets were generated at a rate of 280/sec to 920/sec per syringe. Bead size was 25 µlm to 30 µm, while bead density was 2 beads/nl. The flow tube internal diameter was 2.4 mm. The length of tube for one cycle was 67 cm. Each PCR cycle was timed at 60 sec, and there were 60 cycles plus a pre-heat step taking 2 min. The total time for the PCR reaction was 62 minutes. A 15 um mesh, 25 mm diameter filter was used to capture the beads as they exited the thermal processor.

2.42 million beads were recovered from the filter and then enriched.

Enrichment Protocol Summary:

An enrichment primer (containing both the amplification and sequencing primer regions) is annealed to the beads. The beads are then washed in buffer containing 2M NaCl and Tris pH 7.5 and then mixed with 1 micron biotinylated Seramag beads. This mixture is incubated at RT for three minutes on a rotator and then pelleted at 2,000 rpm in a microcentrifuge. The beads are resuspended by hand vortexing and then incubated on ice for 5 minutes. The mixture is washed on a DYNAL-MPC magnet to remove unannealed material and then NaOH is added to remove the annealed oligo. "Enriched" beads are then recovered by washing in 1× annealing buffer. 2.07 million beads were recovered from the enrichment process.

700,000 of the enriched beads were then sequenced. 414, 557 of these beads had recognizable DNA sequences on them, and 206,000 of those beads had a sequence that averaged 90.5 base pairs long and were mapped to a location on the *E. coli* genome.

Throughout this specification, various patents, published patent applications and scientific references are cited to describe the state and content of the art. Those disclosures, in their entireties, are hereby incorporated into the present specification by reference.

What is claimed is:

1. A method for amplifying genetic material comprising: emulsifying an aqueous fluid comprising a reaction mixture and a plurality of suspended beads in a continuous flow of oil to form a plurality of aqueous microreactors that comprise a smaller dimension relative to a cross section of the continuous flow of oil, wherein a plurality of the microreactors each encapsulate a species of nucleic acid template, a bead capable of capturing the species of nucleic acid template, and sufficient reagents to amplify the species of nucleic acid template, and wherein the step of emulsifying comprises the steps of:
(i) continuously flowing the oil through a cross-flow emulsifier;
(ii) injecting the aqueous fluid into an injection tee operatively coupled to a vibratory anti-clogging device; and
(iii) applying a vibration to the injection tee from the vibratory anti-clogging device to prevent the suspended beads from clogging in a nozzle of the injection tee, thereby forming the aqueous microreactors;
directing the continuous flow of oil comprising the aqueous microreactors across a plurality of stationary controlled temperature zones to amplify the species of nucleic acid template by polymerase chain reaction and immobilize a plurality of the amplified copies on the bead in the aqueous microreactors; and
breaking the emulsion to retrieve one or more of the beads comprising the immobilized amplified species of nucleic acid template.

2. The method according to claim 1, further comprising filtering the continuous flow of oil to collect one or more of the beads comprising the immobilized amplified species of nucleic acid template.

3. The method according to claim 1, wherein the aqueous microreactors have an average size of between approximately 50 to approximately 250 μm in diameter.

4. The method according to claim 1, wherein the species of nucleic acid template are selected from the group consisting of genomic DNA, cDNA, episomal DNA, BAC DNA, and YAC DNA.

5. The method according to claim 1, wherein the beads have a diameter of between approximately 2 microns to approximately 100 microns.

6. The method according to claim 1, wherein the beads are selected from the group consisting of sepharose beads, solid beads, and monodisperse beads.

7. The method of claim 1, wherein a plurality of the aqueous microreactors are evenly distributed along a central area throughout the continuous flow.

8. The method of claim 1, wherein the dimension of the aqueous microreactors is 10 to 50 times smaller than the cross section of the continuous flow.

9. The method of claim 1, wherein the continuous flow is directed via a conduit through a thermal processing device comprising the stationary controlled temperature zones.

10. The method of claim 9, wherein the conduit is selected from the group consisting of a stainless steel conduit, a Polytetrafluoroethylene (PTFE) conduit, and a fused silica conduit.

11. The method of claim 9, wherein the thermal processing device comprises a mandrel, wherein the conduit is helically wound around the mandrel that comprises a first controlled temperature zone and a second controlled temperature zone.

12. The method of claim 9, wherein the thermal processing device comprises alternating sections of the conduit, wherein the sections of conduit are linear and a first section comprises a first controlled temperature zone and a second section comprises a second controlled temperature zone.

13. The method of claim 12, wherein the first and second sections of conduit are positioned in an opposed relationship.

14. The method of claim 1, wherein:
the aqueous microreactors are formed at a controlled rate.

15. The method of claim 14, wherein:
the controlled rate comprises a rate of droplet formation of 500 to 1000 emulsion droplets per second.

16. The method of claim 14, wherein:
the controlled rate comprises a rate of droplet formation of more than 1000 emulsion droplets per second.

17. The method of claim 1, wherein:
the continuous flow of oil flows at a consistent rate.

18. The method of claim 17, wherein:
the consistent rate includes a rate of about 1-10 mls/min.

19. The method of claim 17, wherein:
the consistent rate includes a rate of about 3 mls/min.

20. The method of claim 1, wherein:
the vibratory anti-clogging device is a piezo-electric actuator or an electromagnetic actuator.

* * * * *